United States Patent [19]

Watanabe et al.

[11] Patent Number: 4,698,657

[45] Date of Patent: Oct. 6, 1987

[54] FET TYPE SENSOR AND A METHOD FOR DRIVING THE SAME

[75] Inventors: Masanori Watanabe; Masaya Hijikigawa, both of Nara, Japan

[73] Assignee: Sharp Kabushiki Kaisha, Osaka, Japan

[21] Appl. No.: 697,640

[22] Filed: Feb. 4, 1985

[30] Foreign Application Priority Data

Feb. 10, 1984 [JP] Japan .................................. 59-23598
Mar. 14, 1984 [JP] Japan .................................. 59-49673

[51] Int. Cl.⁴ ............................................ H04L 29/66
[52] U.S. Cl. .................................. 357/25; 357/23.14; 324/71.5
[58] Field of Search ................ 357/25, 23.1, 23.14; 324/71.5; 307/308

[56] References Cited

U.S. PATENT DOCUMENTS

| | | | |
|---|---|---|---|
| 4,020,830 | 5/1977 | Johnson et al. | 357/25 |
| 4,180,771 | 12/1979 | Guckel | 324/71 |
| 4,322,680 | 3/1982 | Janata et al. | 324/71 |
| 4,397,714 | 8/1983 | Janata et al. | 357/25 |
| 4,411,741 | 10/1983 | Janata | 357/25 |
| 4,512,870 | 4/1985 | Kohara et al. | 357/25 |
| 4,514,263 | 4/1985 | Janata | 357/25 |

FOREIGN PATENT DOCUMENTS 1561904  12/1980  United Kingdom .

OTHER PUBLICATIONS

IEEE Transactions on Electron Devices, vol. 29, #1, Jan. 1982, pp. 90–94 by Garverich.

*Primary Examiner*—Andrew J. James
*Assistant Examiner*—Mark Prenty
*Attorney, Agent, or Firm*—Spencer & Frank

[57] ABSTRACT

A field effect transistor-type sensor comprising a field effect transistor device incorporated with a sensitive means exhibiting electric variation due to a physical or chemical interaction with the physical quantity to be detected, wherein an auxiliary electrode for the application of a drift-cancellation voltage to said sensitive means is located on said sensitive means, thereby suppressing the influence of impurities and/or ions contained in the sensitive means and/or the interface between the sensitive means and the field effect transistor device, or impurities and/or ions contaminating the device from the external atmosphere during use thereof, on the operation and/or the output of the field effect transistor device, and maintaining the stable output characteristic over a long period of time.

10 Claims, 4 Drawing Figures

FET TYPE SENSOR AND A METHOD FOR DRIVING THE SAME

BACKGROUND OF THE INVENTION

1. Field of the invention:

The present invention relates to a field effect transistor-type sensor for detecting a variation of the gate operation of a field effect transistor due to a variation of external factors, by a sensitive means formed on the gate insulating film of an MOS- or MIS-field effect transistor.

2. Description of the prior art:

A field effect transistor (hereinafter, referred to as FET)-type sensor, which comprises an FET device incorporated with a sensitive means exhibiting an electric variation of electrostatic capacity, electric conductivity, electrostatic potential, etc., due to a physical or chemical interaction with the physical quantity to be detected, detects the said physical quantity as a variation of the gate operation of the said FET device. Taking advantage of the high input impedance and the amplifying function of the FET device, such an FET type sensor can exhibit a high output, even though its size is extremely small, and thus is advantageous in actual use. Particularly, an FET type sensor which is constructed in such a manner to have a sensitive means on the gate region of the FET device is advantageous practically and economically since the FET device can be small, and a number of devices can be formed on the same substrate. However, such an FET type sensor containing the FET device therein is inferior to an ordinary FET device alone in the operation stability of the FET device. It is also inferior to an FET device with regard to the output stability and the reproducibility of the output characteristic. Depending upon the kind of the FET type sensor required, materials and production processes of the sensitive means are so different that the operation characteristic of the FET device can be remarkably varied. As compared with an ordinary FET device, a large amount of impurities and/or ions are apt to appear in the sensitive means or may contaminate the interface between the sensitive means and the gate insulating film during the formation of the sensitive means on the FET device, causing instability not only in the operation characteristic of the FET device but also in the output characteristic of the FET type sensor. Moreover, since the FET type sensor, which is designed to be used as an atmosphere sensor such as a gas sensor, a moisture sensor, etc., is exposed to an atmosphere, it will be contaminated by impurities in the atmosphere, causing variation and/or deterioration of the FET characteristic and/or deterioration of the sensor itself. Accordingly, an FET type sensor must be provide with an arrangement which will suppress the influence of impurities and/or ions contained in the materials of the sensitive means, or impurities and/or ions contaminating the interface between the sensitive means and the gate insulating film during the formation of the sensitive means on the FET device and/or during operation of the FET device, thereby providing for a stable output characteristic over a long period of time. If such an FET type sensor is designed, a variety of sensors such as gas sensors, moisture sensors, ion sensors, biological sensors, infrared-ray sensors, etc. will be able to be produced in an FET type format. FET type gas sensors, moisture sensors, ion sensors and biological sensors cannot avoid direct interaction of the sensitive means with the atmosphere so that the device therein cannot be covered with a package, etc. Therefore, the above-mentioned problems deriving from the contamination etc. of impurities and/or ions from the outside must be solved for FET type sensors. To solve these problems, a silicon nitride film having a small diffusion coefficient for ions, moisture, etc. has been used as the gate insulating film, or used to cover the surface of the FET device. The resulting FET sensors are, however, still inferior in their output stability over a long period of time.

SUMMARY OF THE INVENTION

The FET type sensor of this invention which overcomes the above-discussed and numerous other disadvantages and deficiencies of the prior art, comprises a field effect transistor device incorporated with a sensitive means exhibiting electric variation due to a physical or chemical interaction with the physical quantity to be detected, wherein an auxiliary electrode for the application of a drift-cancellation voltage to said sensitive means is located on said sensitive means.

The auxiliary electrode is located between the gate insulating film of said field effect transistor device and the sensitive means, and the gate electrode is located on the other surface of said sensitive means.

The sensitive means is a moisture sensitive means, the electrostatic capacity or the electric conductivity of which varies with the absorption and the desorption of water vapor or moisture. The moisture sensitive means is at least one selected from the group consisting of a cellulose derivative film, a vinyl derivative film, an organic or an inorganic solid electrolyte film and a metal oxide film.

The method for driving the FET type sensor of this invention which also overcomes the above-discussed and numerous other disadvantages and deficiencies of the prior art, comprises a field effect transistor device, a sensitive means located between the gate insulating film of said field effect transistor device and the gate electrode, an auxiliary electrode located between said gate insulating film and said sensitive means, and a fixed resistor located between said gate electrode and said auxiliary electrode, wherein said method includes applying a DC voltage and an AC voltage superposed thereon to said gate insulating film and said sensitive means through said gate electrode and said auxiliary electrode while maintaining the resistance of said fixed resistor at a sufficiently high level over the AC impedance of said sensitive means in the frequency of said AC voltage, and obtaining as a detecting signal an AC component resulting from the drain current of said field effect transistor device.

Thus, the invention described herein makes possible the objects of (1) providing an FET type sensor which suppresses the influence of impurities and/or ions contained in the sensitive means and/or the inferface between the sensitive means and the FET device or impurities and/or ions contaminating same from the external atmosphere during the use of the sensor, on the operation and/or the output of the FET device, thereby maintaining the stable output characteristic over a long period of time; (2) providing an FET type sensor which includes a moisture sensor for detecting moisture, a gas sensor for detecting gases, an ion sensor for detecting ions, a biological sensor for detecting organic substances, etc., which maintains stable operation and output characteristics over a long period of time and attains the reproducibility of the characteristics; and (3) providing a method for driving the above-mentioned FET type sensors.

BRIEF DESCRIPTION OF THE DRAWINGS

This invention may be better understood and its numerous objects and advantages will become apparent to those skilled in the art by reference to the accompanying drawings as follows.

DESCRIPTION OF THE PREFERRED EMBODIMENTS

Figure 1:
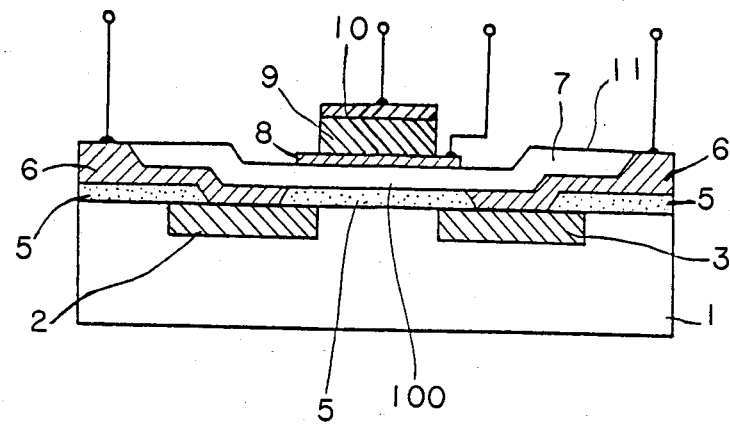
FIG. 1 is a sectional front view showing an FET type sensor according to this invention.

FIG. 1 shows an FET type moisture sensor as an embodiment of the FET type sensor according to this invention, which comprises an FET device 11 incorporated with a moisture sensitive means 9.

The FET device 11 is a MOS-type n-channel FET in which an n-type source 2 and an n-type drain 3 are formed in a row by the diffusion of phosphorus into the surface of a p-type silicon substrate 1. The surface of the silicon substrate 1 is covered by a silicon dioxide film 5 having through-holes for the source 2 and the drain 3. Double layers of the silicon dioxide film (SiO$_2$)5 and a silicon nitride film (Si$_3$N$_4$)7 disposed the silicon substrate 1 form, between the source 2 and the drain 3, a gate insulating film 100. The silicon nitride film 7 serving to protect the FET device 11 covers a portion of the upper face of each of the conductive electrode films 6, which are formed on the silicon substrate 1 and the silicon dioxide film 5, and which come into contact with their respective source 2 and the drain 3 at the ends which extend through the holes in the film 5. On the gate insulating film 100, the moisture sensitive means 9 and a moisture permeable gate electrode film 10 are successively formed. A blocking film 8 made of a conductive film is located between the moisture sensitive means 9 and the silicon nitride film 7. The blocking film 8 serves as an auxiliary electrode which applies a drift-cancellation voltage to the moisture sensitive means 9.

The moisture sensitive means 9 is made of polyvinyl-alcohol or cellulose acetate crystallized by a baking treatment, but is not limited thereto. An organic or inorganic solid electrolyte film, or a metal oxide film such as an aluminium oxide film, etc. can be used therefor. The moisture permeable gate electrode film 10 is made of au gold evaporation film having a thickness of about 100 Å, but is not limited thereto. The blocking film 8 is made of a gold or aluminum evaporation film having a thickness of about 2,000 Å, but is not limited thereto. The sensitive means 9 is not limited to a moisture sensitive means, but may be a gas sensitive means, an ion sensitive means, another chemical substance sensitive means, a heat sensitive means, a light sensitive means, etc. As the FET device, a MIS-type FET can be used.

Figure 2:
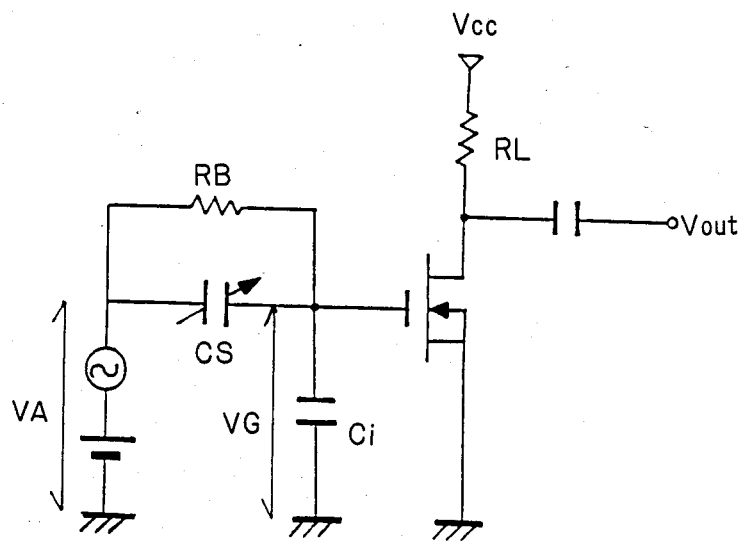
FIG. 2 is an illustration of an equivalent network of the FET type moisture sensor shown in FIG. 1.

FIG. 2 shows an equivalent network of the above-mentioned FET type moisture sensor, wherein references Cs and Ci the are electrostatic capacities of the moisture sensitive means 9 and the double layered gate insulating film 100, respectively; reference R$_L$ is a load resistor connected in series with the drain electrode 6; and reference R$_B$ is a resistor connected in series with the blocking film 8.

The basic operation of the FET type moisture sensor according to this invention is explained as follows: In order to simplify the explanation, the case where the moisture sensitive means 9 is directly formed on the gate insulating film 100 without the blocking film 8, that is, the resistor RB is omitted in the equivalent network in FIG. 2, is described, first.

Given that the voltage to be applied to the moisture permeable gate electrode film 10 is V$_A$ and the threshold voltage of the FET device 11 is V$_{th}$, the drain current I$_D$ can be represented by the following equation (1):

$$I_D=(\beta/2)(V_A-V_{th})^2, \beta=(\mu nCW/L) \tag{1}$$

wherein $\mu$n is a carrier mobility; L and W are the channel length and the channel width of the FET device, respectively; and C is an electrostatic capacity, in the case where an electrostatic capacity Ci of the gate insulating film is connected in series with an electrostatic capacity C$_s$ of the moisture sensitive means 9, and is represented by the equation (2):

$$C=(CsCi/Cs+Ci) \tag{2}$$

Thus, given that V$_A$ is a constant value, moisture can be detected a variation of the drain current I$_D$ with the variation of the electrostatic capacity C$_s$ of the moisture sensitive means 9 depending upon the moisture of the external atmosphere.

Since a DC potential difference exists between both surfaces of the moisture sensitive means 9, impurities and/or ions contained in the moisture sensitive means 9 migrate by the action of an electric field, thereby attaining a rearrangement and/or a localization thereof which have a remarkable effect on the device characteristic in the channel region of the FET device, causing a variation of the threshold voltage V$_{th}$ and the drift of the operation characteristic i.e., operating point, of the FET device, and further causing a drift of the output signal as a moisture sensor. In the case where impurities and/or ions are contained in the interface between the moisture sensitive means 9 and the moisture permeable gate electrode film 10 and/or the interface between the moisture sensitive means 9 and the gate insulating film 100, the same phenomenon as the above-mentioned occurs as well. As described before, the contamination by impurities and/or ions from the external atmosphere into the device is unavoidable, and accordingly the solution of such problems is of great importance in providing the desired FET type moisture sensor.

In order to solve such problems and thereby provide an FET type moisture sensor which can operate stably over a long period of time, an FET type moisture sensor according to this invention comprises a conductive blocking film 8 located between the moisture sensitive means 9 and the gate insulating film 100, as shown in FIG. 1. The blocking film 8 is connected with the moisture permeable gate electrode film 10 on the moissensitive means 9 by the resistor $R_B$ as shown in FIG. 2. A voltage $V_A$, which is composed of a DC voltage $V_A$ (DC) and an AC voltage of frequency f superposed thereon, is applied to the gate insulating film 100 and the moisture sensitive means 9 through the moisture permeable gate electrode film 10 and the blocking film 8 to thereby drive this FET type moisture sensor. In the case where the DC voltage $V_A$ (DC) is smaller than the withstand voltage of the gate insulating film 100 and a leakage current does not occur through the gate insulating film 100, the DC voltage component $V_G$(DC) of the effective gate voltage $V_G$ applied to the blocking film 8 becomes equal to the DC voltage $V_A$ (DC), resulting in no DC potential difference between both surfaces of the moisture sensitive means 9, so that the above-mentioned phenomenon that impurities and/or ions migrate within the moisture sensitive means 9 causing their rearrangement and/or localization can be suppressed and, additionally, the diffusion of these impurities and/or ions into the gate insulating film 100 can be suppressed because of the incorporation of the blocking film 8. Since the DC voltage $V_G$(DC) is equal to the DC voltage $V_A$ (DC), this FET type moisture sensor cannot, of course, operate as a moisture sensor by the application of the DC voltage $V_A$ (DC) alone. The DC voltage $V_A$ (DC) functions to give an optimum bias voltage in the $I_D-V_G$ characteristic of the FET device.

In order that the FET type moisture sensor operates as a moisture sensor, that is, it detects the variation of an electrostatic capacity $C_s$ of the moisture sensitive means due to the moisture in an atmosphere, an AC voltage $V_A$ (AC) is essential.

In the case where the resistor $R_B$, having a resistance value which is sufficiently great as compared with the impedance $(2\pi f C_S)^{-1}$ of the moisture sensitive means at a frequency f, is connected to the blocking film 8 and the moisture permeable gate electrode film 10, the resistance of resistor $R_B$ is negligible and the AC voltage component $V_G$ (AC) of the gate voltage $V_G$ can be represented by the equation (3):

$$V_G(AC) = C_S/(C_S + C_i) V_A(AC) \tag{3}$$

This indicates that since $V_G$ (AC) varies with the values of the electrostatic capacity $C_s$ of the moisture sensitive means at the application of $V_A$ (AC) with a given amplitude, the output signal required for a moisture sensor can be detected as the AC amplitude of the drain current $I_D$. Thus, the modulation of an electric current flowing from the source 2 to the drain 3 while applying $V_A$ (AC) to the gate electrode film 10, can be detected by the conductive electrode film 6 as a detecting signal.

Figure 3:
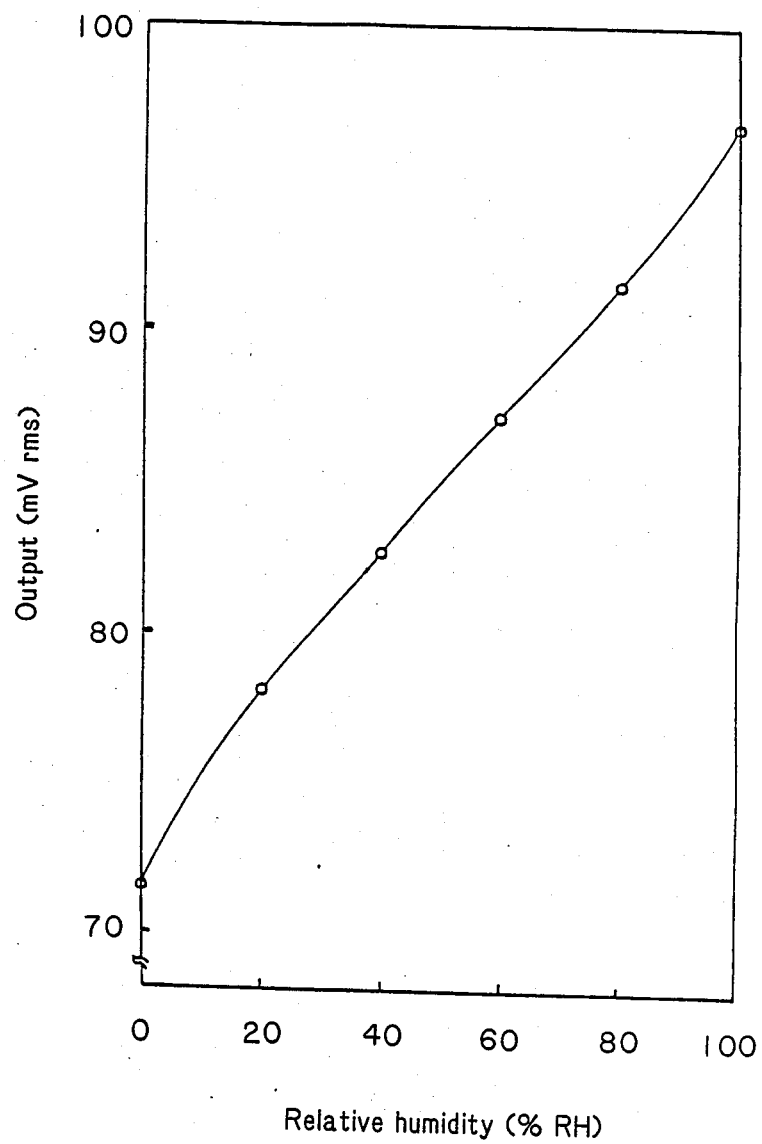
FIG. 3 is a chracteristic curve showing the relationship between the output and the relative humidity of the moisture sensor in FIG. 1.

FIG. 3 shows the output i.e., the relative humidity characteristic experimentally measured, while the above-mentioned FET type moisture sensor operated under the conditions that the moisture sensitive means 9 was made of a baked cellulose acetate film; the values of the fixed resistors $R_B$ and $R_L$, respectively, are 10 MΩ and 1 KΩ; that $V_A$ (DC) is 5 V; and that $V_A$ (AC) is 100 mV rms (10 KHz).

Figure 4:
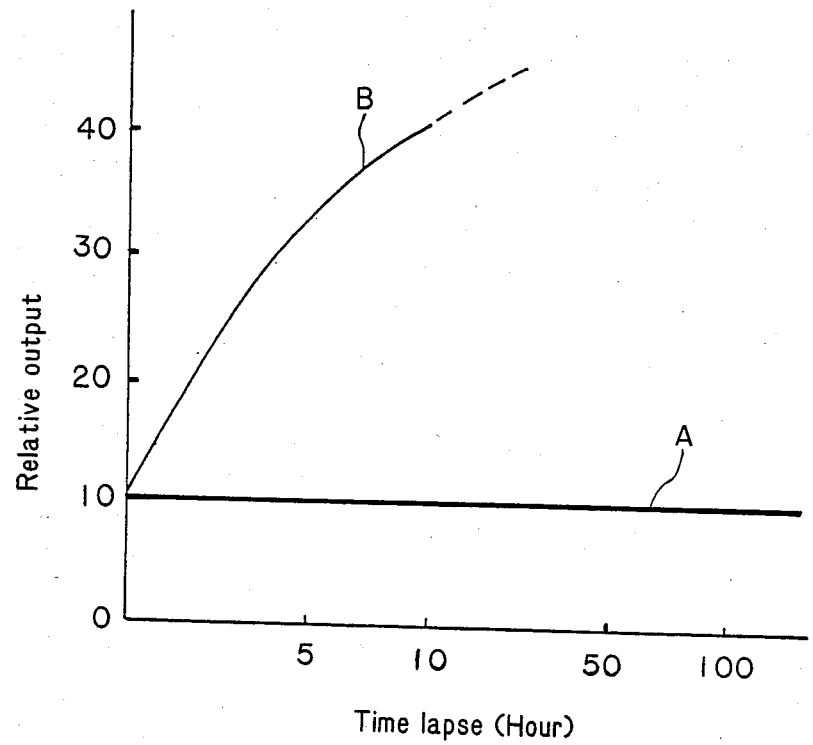
FIG. 4 show two characteristic curves, with curve A showing the drift of the experimental output value of the FET type moisture sensor of FIG. 1 and with the other curve B showing the drift of the experimental output value of a control FET type moisture sensor containing no blocking film.

In order to reveal the output stability of the above-mentioned FET type moisture sensor, the relationship between the time for which the FET device was allowed to stand in an atmosphere having a relative humidity of 60% and the output of the FET type moisture sensor was examined and is shown in FIG. 4, wherein the characteristic curve A shows the drift of the output of the test sensor containing the blocking film 8, while the characteristic curve B shows the drift of the output of the control sensor containing no blocking film 8. Both sensors were subjected to examination under the same operating and measuring conditions, and their outputs, respectively, were expressed by a relative value on the basis of the initial output value. FIG. 4 indicates that the use of the blocking film 8 is significantly effective to maintain the output of the FET type moisture sensor stably for a long period of time and that the drain current $(I_D)$—drain voltage $(V_{DS})$ characteristic, and the drain current $(I_D)$—the gate voltage $(V_G)$ characteristic, etc. of the FET device are stable, do not drift and exhibit excellent reproducibility. On the contrary, in the case where the blocking film 8 is not employed as shown by the characteristic curve B in FIG. 4, both the $I_D-V_{DS}$ characteristic and the $I_D-V_G$ characteristic of the FET device exhibit great drift and are extremely inferior in reproducibility. Moreover, it can be observed that the $I_D-I_{DS}$ characteristic and/or the $I_D-V_G$ characteristic are greatly different from the initial characteristic even when the ON-OFF operation or the polarity at the applicaiton of $V_G$ is reversed. This phenomenon indicates that the migration and the distribution (rearrangement) of impurities and/or ions in the moisture sensitive means and/or the interface between the moisture sensitive means and the gate insulating film by the action of an electric field have remarkable effect on the characteristics of the FET device.

It is understood that various other modifications will be apparent to and can be readily made by those skilled in the art without departing from the scope and spirit of this invention. Accordingly, it is not intended that the scope of the claims appended hereto be limited to the description as set forth herein, but rather that the claims be construed as encompassing all the features of patentable novelty which reside in the present invention, including all features which would be treated as equivalents thereof by those skilled in the art to which this invention pertains.

What is claimed is:

1. In a field effect transistor-type sensor including an insulated gate field effect transistor device incorporated with a sensitive means for exhibiting a variation in its dielectric constant due to a physical or chemical interaction with the quantity to be detected, said sensitive means being located between the gate insulating film and the gate electrode of said field effect transistor device; the improvement comprising:
   an auxiliary electrode located between said gate insulating film and said sensitive means; and
   a resistance means connected to said auxiliary electrode and through which a DC bias voltage for stabilizing the operating point of said field effect transistor device is applied to said auxiliary electrode.

2. A field effect transistor-type sensor according to claim 1 wherein said sensitive means is a moisture sensitive means, the electrostatic capacity of which varies with the absorption and the desorption of water vapor or moisture.

3. A field effect transistor-type sensor according to claim 3, wherein said moisture sensitive means is at least one selected from the group consisting of a cellulose derivative film, a vinyl derivative film, an organic or an inorganic solid electrolyte film and a metal oxide film.

4. A method for driving a field effect transistor-type sensor comprising an insulated gate field effect transistor device, a sensitive means located between the gate insulating film of said field effect transistor device and the gate electrode, an auxiliary electrode located between said gate insulating film and said sensitive means, and a resistance means connected to said auxiliary electrode, wherein said method includes: applying a DC voltage having an AC voltage superposed thereon to said gate insulating film and said sensitive means through said gate electrode and said resistance means, respectively while providing a resistance value for said resistance means which is substantially greater than the AC impedance of said sensitive means at the frequency of said AC voltage; and detecting the amplitude of the AC component of the drain current of said field effect transistor device.

5. A field effect transistor-type sensor according to claim 1 wherein said sensitive means is a layer of dielectric material.

6. A field effect transistor type sensor according to claim 5 wherein said resistance means is connected between said gate electrode and said auxiliary electrode.

7. A field effect transistor-type sensor according to claim 6 wherein said resistance means is a fixed resistor.

8. A field effect transistor-type sensor according to claim 6 wherein the resistance value of said resistance means is substantially greater than the AC inmedance of said sensitive means at a frequency f; and further comprising means for applying a DC voltage having an AC voltage of said freguency f superposed thereon to said gate electrode; and means for detecting the amplitude of the AC component of the drain current of said field effect transistor device as a measure of the variation of the electrosatic capacity of said sensitive means.

9. A field effect transistor-type sensor comprising in combination: a semiconductor body having spaced source and drain regions formed therein adjacent one surface to define a channel region therebetween; an insulating layer covering said surface and having openings above said source and drain regions; source and drain electrodes contacting said source and drain regions, respectively, via the respective said openings; an auxiliary electrode disposed on said insulating layer over said channel region; a sensitive insulating film, which exhibits a variation in its dielectric constant due to a physical or chemical interaction with a quantity to be detected, disposed on said auxiliary electrode; a gate electrode disposed on the outer surface of said sensitive insulating film; means for applying a DC voltage having an AC voltage superimposed thereon to said gate electrode; a resistance connected between said auxiliary electrode and said gate electrode, said resistance having a value, which is substantially greater than the AC impedance of said sensitive insulating film at the frequency of said AC voltage; and means for detecting the amplitude f of the AC component of the drain current of said field effect transistor.

10. A field effect transistor as defined in claim 9 wherein said resistance is a fixed resistor.

* * * * *